(12) United States Patent
Iannotti et al.

(10) Patent No.: US 9,198,732 B2
(45) Date of Patent: Dec. 1, 2015

(54) APPARATUS AND METHOD FOR DICTATING AT LEAST ONE OF A DESIRED LOCATION AND A DESIRED TRAJECTORY FOR ASSOCIATION OF A LANDMARK WITH A PATIENT TISSUE

(71) Applicant: THE CLEVELAND CLINIC FOUNDATION, Cleveland, OH (US)

(72) Inventors: Joseph P. Iannotti, Strongsville, OH (US); Wael K. Barsoum, Bay Village, OH (US); Jason A. Bryan, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 185 days.

(21) Appl. No.: 13/733,346

(22) Filed: Jan. 3, 2013

(65) Prior Publication Data

US 2013/0172898 A1    Jul. 4, 2013

Related U.S. Application Data

(60) Provisional application No. 61/583,087, filed on Jan. 4, 2012.

(51) Int. Cl.
*A61B 17/17* (2006.01)
*A61B 19/00* (2006.01)
*A61B 17/34* (2006.01)

(52) U.S. Cl.
CPC ............. *A61B 19/46* (2013.01); *A61B 17/1739* (2013.01); *A61B 17/3403* (2013.01);
(Continued)

(58) Field of Classification Search
CPC ........... A61B 17/8897; A61B 17/1742; A61B 17/1746; A61B 2017/90; A61B 2017/1778; A61B 17/88; A61B 17/17; A61B 17/1717; A61B 17/1721; A61B 5/1072; B23Q 17/2216; B23Q 17/2225; B25H 1/0078

USPC ........ 606/86 R, 87, 96–98, 102, 104; 33/512, 33/638
See application file for complete search history.

(56) References Cited

U.S. PATENT DOCUMENTS

| | | | | |
|---|---|---|---|---|
| 2,483,060 A | * | 9/1949 | Niedelman et al. | 408/112 |
| 2,635,348 A | * | 4/1953 | Jones | 33/638 |

(Continued)

FOREIGN PATENT DOCUMENTS

| | | |
|---|---|---|
| EP | 1046377 A2 | 10/2000 |
| EP | 2168507 A2 | 3/2010 |

(Continued)

OTHER PUBLICATIONS

International Search Report and Written Opinion for PCT/US2013/030088, Int'l filed Jan. 3, 2013, mailed Mar. 22, 2013, pp. 1-13.

*Primary Examiner* — Matthew Lawson
*Assistant Examiner* — Amy Sipp
(74) *Attorney, Agent, or Firm* — Tarolli, Sundheim, Covell & Tummino LLP

(57) ABSTRACT

An apparatus for transferring location and/or trajectory information from a reference surface to a patient tissue surface for guiding placement of a landmark includes a landmark guiding structure. At least two locating feet are provided, each being laterally spaced from, and indirectly connected to, the landmark guiding structure. A holdaway structure is connected to each locating foot and to the landmark guiding structure. The landmark guiding structure is placed in desired location and/or a desired trajectory with respect to the reference surface. Each locating foot is adjusted into guiding contact with a particular portion of the reference surface. Each locating foot is maintained in the guiding contact position, and the apparatus is placed with each locating foot in guiding contact with a particular portion of the patient tissue surface. A method of transferring location and/or trajectory information from a reference surface to a patient tissue surface is also disclosed.

23 Claims, 7 Drawing Sheets

(52) U.S. Cl.
CPC ............... *A61B19/201* (2013.01); *A61B 17/17* (2013.01); *A61B 17/1746* (2013.01); *A61B 17/1757* (2013.01); *A61B 17/1764* (2013.01); *A61B 19/5244* (2013.01); *A61B 2017/1775* (2013.01); *A61B 2017/1778* (2013.01); *A61B 2017/1782* (2013.01); *A61B 2017/3407* (2013.01); *A61B 2019/505* (2013.01); *A61B 2019/5487* (2013.01)

(56) References Cited

U.S. PATENT DOCUMENTS

| | | | | |
|---|---|---|---|---|
| 3,464,295 | A * | 9/1969 | Gallion | 408/112 |
| 4,366,940 | A * | 1/1983 | Vargas | 248/542 |
| 4,948,304 | A * | 8/1990 | Kobayashi | 408/16 |
| 5,112,337 | A | 5/1992 | Paulos et al. | |
| 5,141,512 | A * | 8/1992 | Farmer et al. | 606/87 |
| 5,141,513 | A * | 8/1992 | Fortune et al. | 606/96 |
| 5,334,192 | A | 8/1994 | Behrens | |
| 5,752,962 | A * | 5/1998 | D'Urso | 606/130 |
| 6,893,447 | B2 * | 5/2005 | Dominguez et al. | 606/130 |
| 8,801,725 | B2 * | 8/2014 | Ritter et al. | 606/102 |
| 2007/0106305 | A1 * | 5/2007 | Kao et al. | 606/130 |
| 2008/0221581 | A1 * | 9/2008 | Shoham | 606/96 |
| 2009/0062809 | A1 * | 3/2009 | Steiner | 606/102 |
| 2010/0042111 | A1 * | 2/2010 | Qureshi et al. | 606/130 |
| 2010/0082035 | A1 * | 4/2010 | Keefer | 606/91 |
| 2011/0035013 | A1 * | 2/2011 | Winslow et al. | 623/19.13 |

FOREIGN PATENT DOCUMENTS

| | | |
|---|---|---|
| WO | 95/13758 A1 | 5/1995 |
| WO | 02/24095 A1 | 3/2002 |
| WO | 2011/063281 A1 | 5/2011 |

* cited by examiner

APPARATUS AND METHOD FOR DICTATING AT LEAST ONE OF A DESIRED LOCATION AND A DESIRED TRAJECTORY FOR ASSOCIATION OF A LANDMARK WITH A PATIENT TISSUE

RELATED APPLICATION

This application claims priority from U.S. Provisional Application No. 61/583,087, filed 4 Jan. 2012, the subject matter of which is incorporated herein by reference in its entirety.

TECHNICAL FIELD

The present invention relates to an apparatus and method for dictating at least one of a desired location and a desired trajectory for association of a landmark with a patient tissue and, more particularly, to an apparatus and method for transferring at least one of location and trajectory information from a reference surface to a patient tissue surface for guiding placement of a landmark.

BACKGROUND OF THE INVENTION

In the installation of a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault.

Because the shoulder prosthesis is normally provided to correct a congenital or acquired defect of the native shoulder joint, the glenoid vault often exhibits a pathologic, nonstandard anatomic configuration. A surgeon must compensate for such pathologic glenoid vault anatomy when implanting the glenoid component in striving to achieve a solid anchoring of the glenoid component into the glenoid vault. Detailed preoperative planning, using two- or three-dimensional internal images of the shoulder joint, often assists the surgeon in compensating for the patient's anatomical limitations. During the surgery, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. Again, a guide pin may be temporarily or permanently placed into the exposed bone surface to help orient the surgeon and thereby enhance the accuracy and efficiency of the surgical procedure.

A carefully placed guide pin or other landmark, regardless of the reason provided, will reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, an apparatus for transferring at least one of location and trajectory information from a reference surface to a patient tissue surface for guiding placement of a landmark is described. The reference surface substantially replicates three-dimensionally at least a portion of the patient tissue surface. A landmark guiding structure is provided. At least two locating feet are provided. Each locating foot is laterally spaced from, and indirectly connected to, the landmark guiding structure. A holdaway structure is connected to each locating foot. Each holdaway structure is adjustably connected to the landmark guiding structure to indirectly and adjustably attach the locating foot to the landmark guiding structure in a spaced-apart relationship therewith. A manipulation handle is connected to the landmark guiding structure. The landmark guiding structure is placed in at least one of a desired location and a desired trajectory with respect to the reference surface. Each locating foot is adjusted relative to the landmark guiding structure, via adjustment of the holdaway structure, into guiding contact with a particular portion of the reference surface. Each locating foot is maintained in the guiding contact position, the apparatus is removed from the reference surface, and the apparatus is placed with each locating foot in guiding contact with a particular portion of the patient tissue surface corresponding to a particular portion of the reference surface such that at least one of the desired location and desired trajectory of the landmark guiding structure at the reference surface is replicated by the landmark guiding structure at the patient tissue surface.

In an embodiment of the present invention, a method of transferring at least one of location and trajectory information from a reference surface to a patient tissue surface is described. The reference surface substantially replicates at least a portion of the patient tissue surface. A landmark guiding structure is provided. At least two locating feet are provided, each locating foot being laterally spaced from, and indirectly connected to, the landmark guiding structure. A holdaway structure is connected to each locating foot. Each holdaway structure is adjustably connected to the landmark guiding structure to indirectly and adjustably attach the locating foot to the landmark guiding structure in a spaced-apart relationship therewith. A manipulation handle connected to the landmark guiding structure is provided. The landmark guiding structure is placed in at least one of a desired location and a desired trajectory with respect to the reference surface. Each locating foot is adjusted relative to the landmark guiding structure, via adjustment of the holdaway structure, into guiding contact with a particular portion of the reference surface. Each locating foot is maintained in the guiding contact position. The apparatus is removed from the surface. The apparatus is placed with each locating foot in guiding contact with a particular portion of the patient tissue surface corresponding to a particular portion of the reference surface such that at least one of the desired location and desired trajectory of the landmark guiding structure at the reference surface is replicated by the landmark guiding structure at the patient tissue surface.

In an embodiment of the present invention, an adjustable instrument for dictating at least one of a desired location and a desired trajectory for association of a landmark with a patient tissue is described. An elongate landmark guiding structure has longitudinally spaced proximal and distal guiding ends separated by a guiding shaft. At least two holdaway structures are adjustably connected to the landmark guiding structure for longitudinal motion relative to the landmark guiding structure. At least two locating feet are provided, each locating foot being laterally spaced from the landmark guiding structure. Each locating foot is directly connected to a holdaway structure and, via the holdaway structure, is indirectly connected to the landmark guiding structure. Each holdaway structure is adjustable to place the locating foot associated therewith into a predetermined locating foot position such that, when the locating feet have all achieved the predetermined locating foot positions, contact between each of the locating feet and corresponding predetermined portions of the patient tissue results in an orientation of the landmark guiding structure with respect to the patient tissue which dictates at least one of the desired location and the desired trajectory for association of the landmark with the patient tissue.

BRIEF DESCRIPTION OF THE DRAWINGS

For a better understanding of the invention, reference may be made to the accompanying drawings, in which.

DESCRIPTION OF EMBODIMENTS

Figure 1:
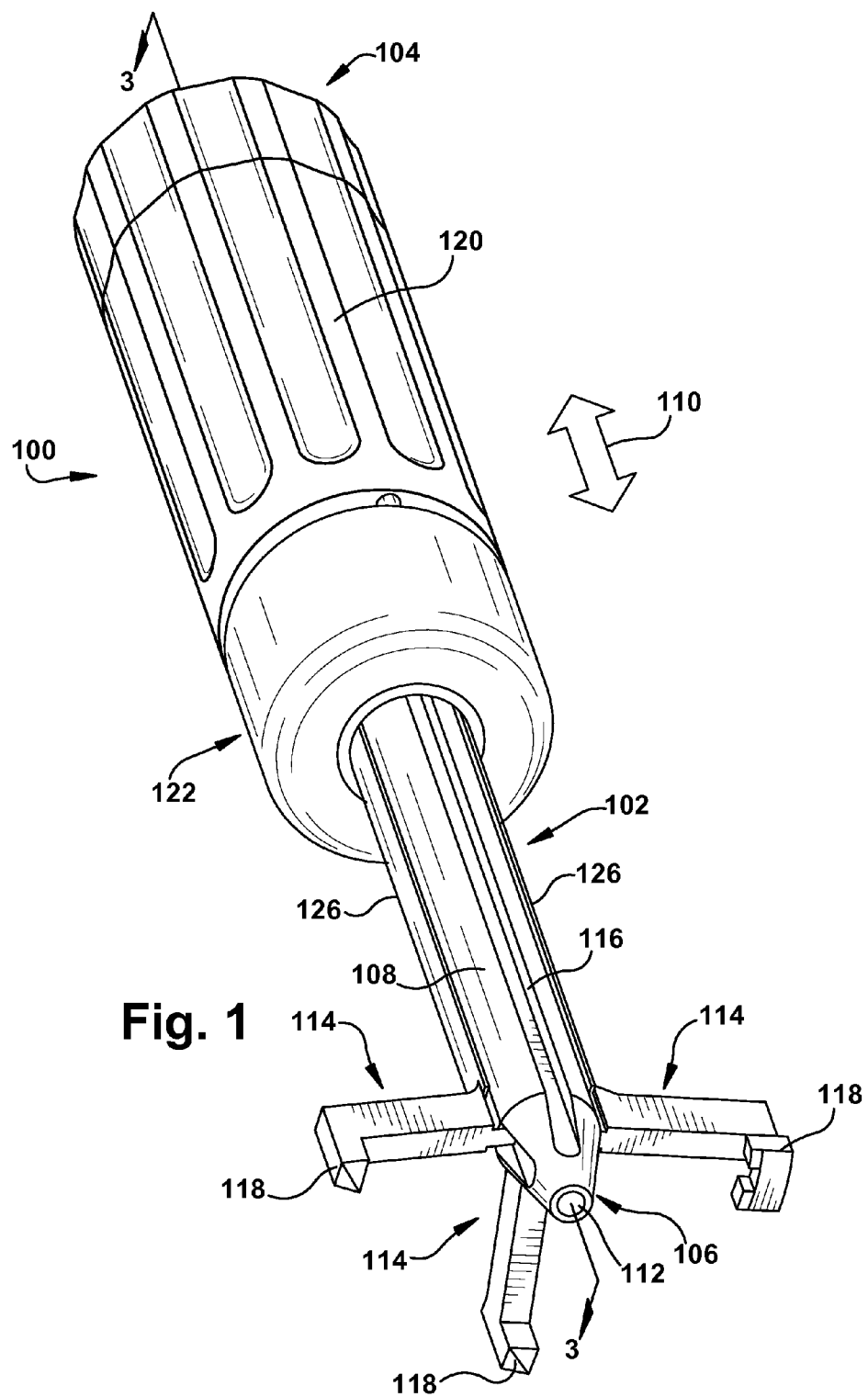
FIG. 1 is a partial perspective side view of an embodiment of the present invention.

In accordance with the present invention, FIG. 1 depicts an adjustable instrument 100 for dictating at least one of a desired location and a desired trajectory for association of a landmark with a patient tissue. The instrument 100 includes an elongate landmark guiding structure 102 having longitudinally spaced proximal and distal guiding ends 104 and 106, respectively, separated by a guiding shaft 108. The longitudinal direction is shown in FIG. 1 by longitudinal arrow 110, and a lateral direction is described herein as being within a plane perpendicular to the longitudinal direction.

As can be seen in FIG. 1, a guiding throughbore 112 extends longitudinally through the landmark guiding structure 102. Here, the throughbore 112 is a simple core or lumen running through the center of the landmark guiding structure 102, but it is also contemplated that the throughbore may be laterally offset from a center of the landmark guiding structure 102, may be an open groove or other laterally accessible feature of the guiding structure, or may have any other suitable structure for interacting with a landmark in a specific application of the present invention.

At least two holdaway structures 114 (three shown in FIG. 1) are adjustably connected to the landmark guiding structure 102 and configured for longitudinal motion relative to the landmark guiding structure. For a particular application of the present invention, holdaway structure(s) 114 having any number, configuration, arrangement, symmetry (or asymmetry), or any other qualities may be provided and can be readily configured by one of ordinary skill in the art for a particular application of the present invention. In the embodiment of FIG. 1, the holdaway structures 114 are each connected to the landmark guiding structure 102 via an interlocking (tongue and groove) arrangement with a groove 116 on the guiding shaft 108. In other words, at least a portion of each holdaway structure 114 is shown in FIG. 1 as riding movably within a corresponding groove 116 to allow the holdaway structures 114 to be moved longitudinally toward and away from the distal guiding end 106 of the landmark guiding structure 102. There may be fewer or more grooves 116 than holdaway structures 114 for a particular application of the present invention, as desired, with some grooves optionally having more than one holdaway structure, and other grooves optionally having no holdaway structures, associated therewith.

Figure 2:
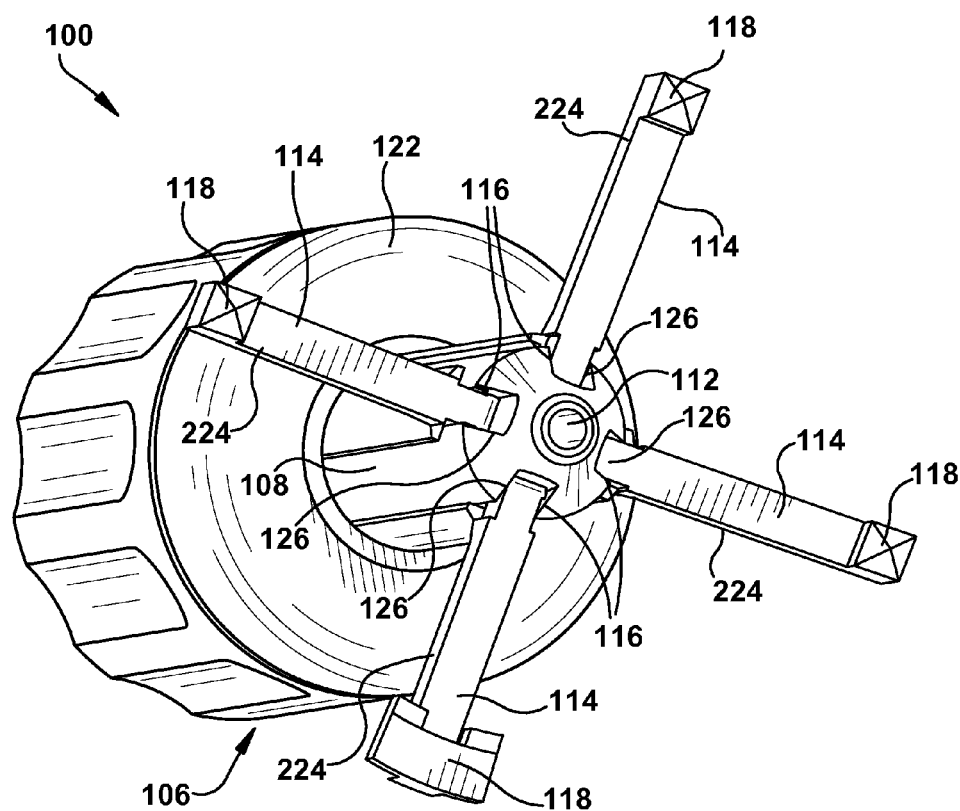
FIG. 2 is a perspective bottom view of the embodiment of FIG. 1.

At least two locating feet 118 (three shown in FIG. 1) are laterally spaced from the landmark guiding structure 102. Each locating foot 118 is laterally spaced from the landmark guiding structure 102. Each locating foot 118 is directly connected to a holdaway structure 114 and is, via the holdaway structure, indirectly connected to the landmark guiding structure 102. The connection between a particular holdaway structure 114, an associated locating foot 118, and the landmark guiding structure 102 may be adjustable to allow the holdaway structure to provide or facilitate relative longitudinal motion between locating foot and the landmark guiding structure. As with the holdaway structure(s) 114, there may be locating feet 118 having any number, configuration, arrangement, symmetry (or asymmetry), or any other qualities, and one of ordinary skill in the art can readily provide a desired set of locating feet 118 for a particular application of the present invention. There may be none, one, or more than one locating foot/feet 118 provided to a single holdaway structure 114. The locating feet 118 may have any configuration as desired (e.g., including rough "gripping" portions, tapered points, or any other structures), and the locating feet 118 associated with a single instrument 100 need not be identical or even similar in any physical property. Optionally, and as shown in FIG. 2, at least four locating feet 118 may be laterally (though not necessarily symmetrically or evenly) spaced from each other about the guiding shaft 108. Each locating foot 118 may be, during certain portions of the operation of the instrument 100 (as will be described below), substantially longitudinally adjacent to, and laterally spaced from, the distal guiding end 106 of the landmark guiding structure 102 for a particular application of the present invention.

A manipulation handle 120 of any suitable type may be connected to the landmark guiding structure 102 for grasping by a user. The manipulation handle 120 shown in FIG. 1 is similar to a screwdriver handle, but it is contemplated that any other type of handle (not shown) such as, but not limited to, a t-handle, orthopedic or "pistol grip" handle, or the like, may be provided for a particular application of the present invention.

Figure 3:
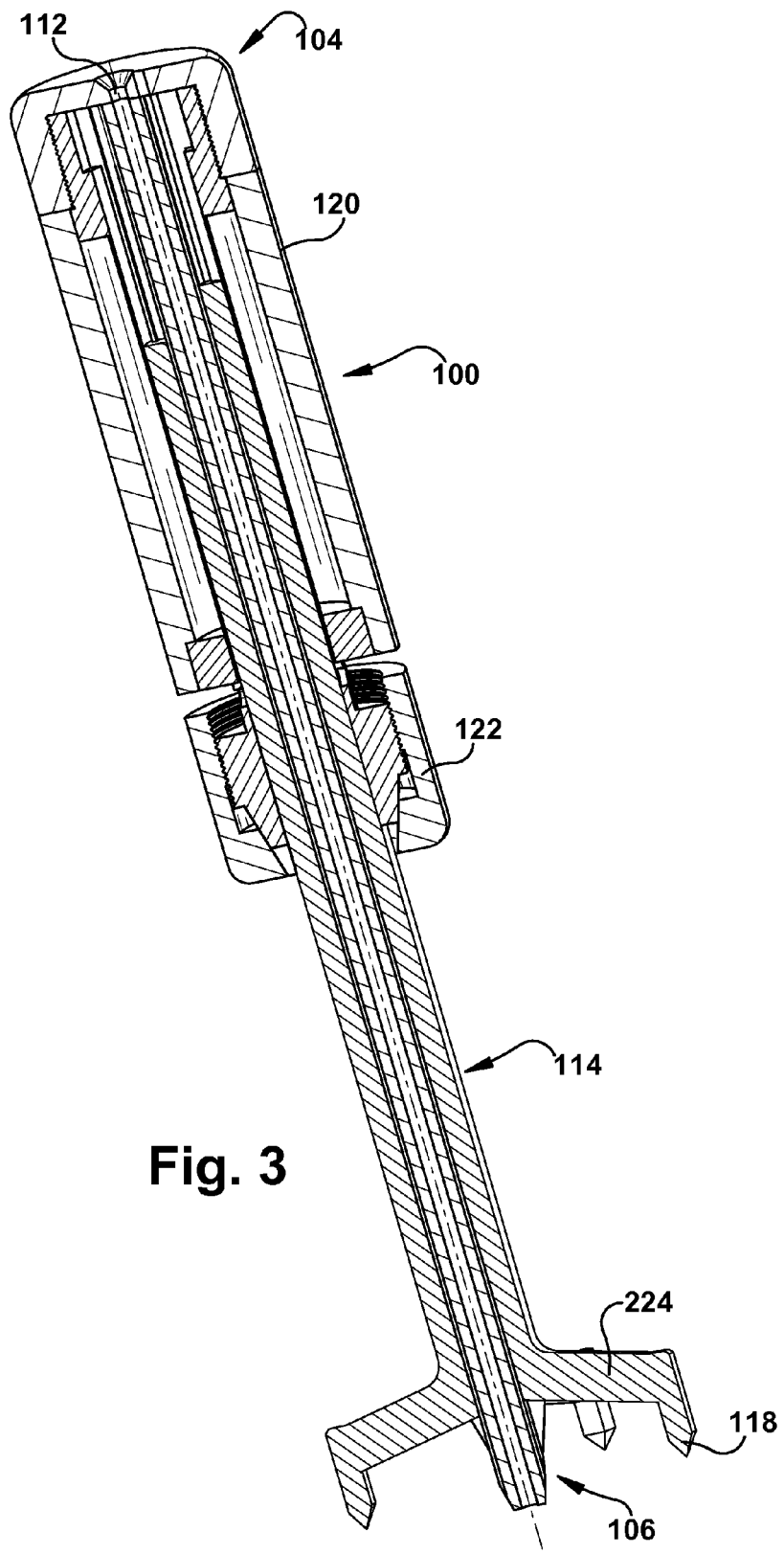
FIG. 3 is a cross-sectional side view taken along line 3-3 of FIG. 1.

A locking mechanism 122 may be provided to the instrument 100 to selectively maintain at least one locating foot 118 in a desired position (as will be described below) during use—generally involving manipulation and/or relocation—of the instrument 100. As shown in FIGS. 1 and 3, the locking mechanism 122 takes the form of a locking collar, which can be turned to tighten simultaneously or concurrently about the guiding shaft 108 and the holdaway structures 114, once the holdaway structures have been adjusted as desired, to prevent relative motion between the locating feet 118 and the landmark guiding structure 102.

Figure 4:
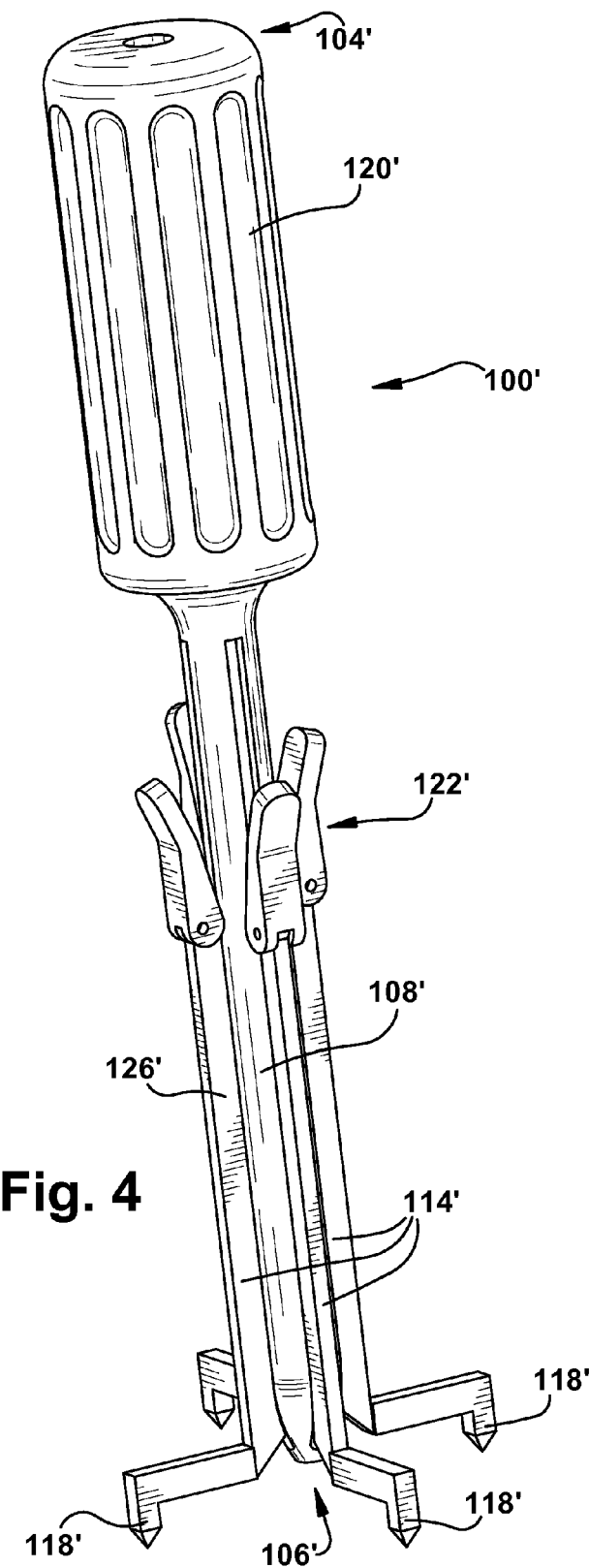
FIG. 4 is a side view of the embodiment of FIG. 1 in an alternate configuration.
Figure 5:
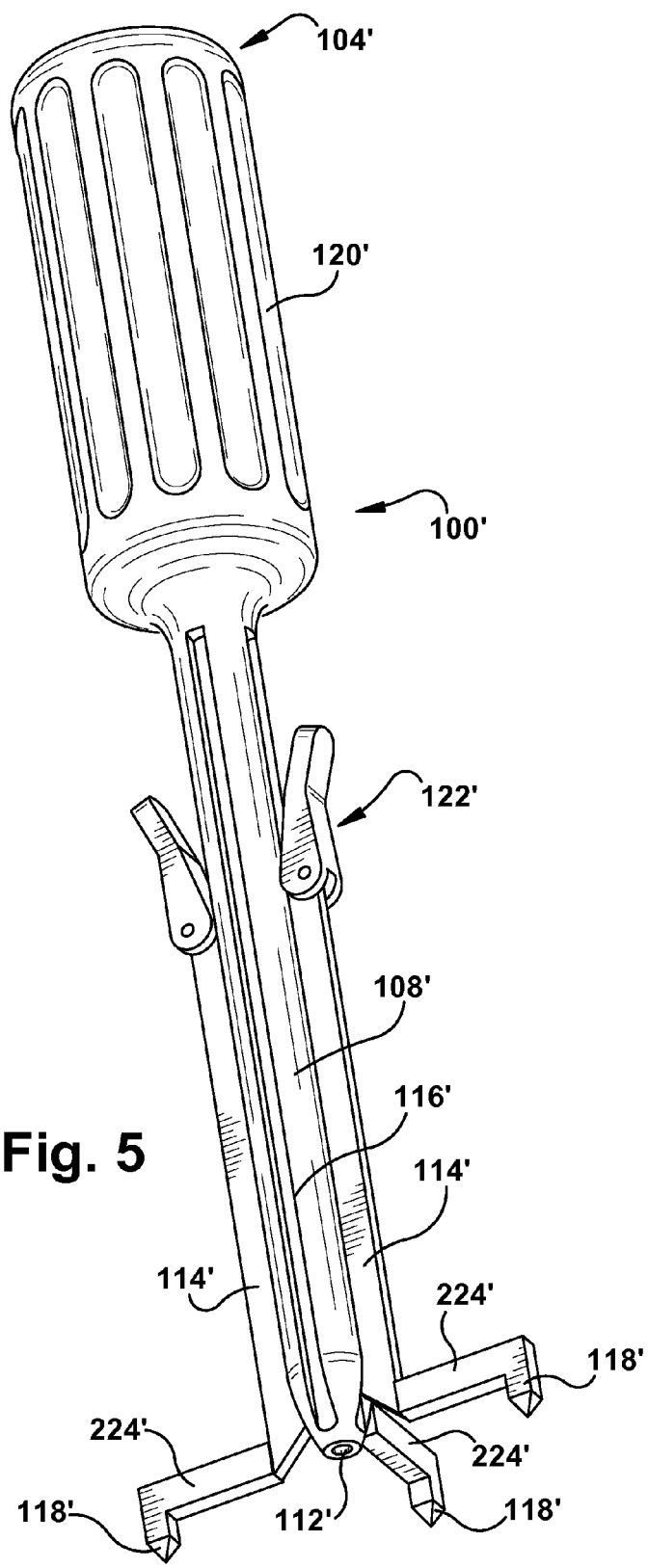
FIG. 5 is a partial perspective side view of the embodiment of FIG. 4.

In contrast, FIGS. 4 and 5 depict an instrument 100' which is substantially similar to that of FIGS. 1-3, other than the configuration of the locking mechanism 122. In FIGS. 4 and 5, the locking mechanism 122' takes the form of a plurality of cam-locks, each associated with a different holdaway structure 114'. These cam-lock structures are operated in a known manner, in which a lever carried by the holdaway structure 114' is lifted or pushed to either squeeze a cam laterally inward against the guiding shaft 108' or to pull the holdaway structure 114' laterally outward and into a frictional fit with the groove 116'. Regardless of the type of operation, the cam-locks shown in FIGS. 4 and 5 can be used to individually prevent relative motion between the holdaway structures 114' and the guiding shaft 108', once the holdaway structures have been adjusted as desired, to prevent relative motion between the locating feet 118' and the landmark guiding structure 102'. Accordingly, unlike the instrument 100 shown in FIGS. 1-3, the holdaway structures 114' of the instrument 100' of FIGS. 4 and 5 can be individually adjusted and tightened. Alternately, though not shown, a unitary cam-lock could also or instead be provided to simultaneously or concurrently actuate the locking mechanism 122' of the instrument 100' of FIGS. 4 and 5. One of ordinary skill in the art could readily provide a suitable reversible or permanent locking mechanism 122 having any desired format, configuration, or structure for a particular application of the present invention.

Returning to the instrument 100 as shown in FIGS. 1-3, the interface between the guiding shaft 108, the holdaway structures 114, and the locating feet 118 is shown in detail in FIG. 2. At least one originally provided locating foot 118 (optionally along with an associated holdaway structure 114) can be removable from the instrument 100 and thereby be interchangeable with a separately provided auxiliary locating foot (not shown) having some physical property that differs from the locating foot being replaced. For example, in the instance where a locating foot 118 has a squared-off profile, the user may wish to instead use an auxiliary locating foot having a pointed or sharpened profile. As another example, and as shown in FIG. 2, the locating foot 118 and/or the holdaway structure 114 may include a bridge region 224 which serves to space the locating foot 118 laterally from the guiding shaft 108, and the user may wish to instead use a locating foot and/or holdaway structure having a longer or shorter bridge structure, to space the auxiliary locating foot a different lateral distance than was the originally provided locating foot being replaced.

It should be noted that the bridge region 224 of the embodiments shown in the Figures is not definitively associated with either the locating foot 118 or the holdaway structure 114, since these two structures are shown as being integrally formed as one piece. It is contemplated, however, that—particularly when separated locating feet 118 and holdaway structures 114 are provided—any provided bridge regions 224 may, contrary to the depicted arrangement, be clearly associated with one or the other of the locating foot or holdaway structure and separate from the other one. Whether via a bridge region 224 or another physical construct, however, the holdaway structure 114 will be characterized in the below discussion as the portion of the instrument 100 which provides the described lateral spacing between at least one locating foot 118 and the landmark guiding structure 102, for clarity.

As previously alluded to, and as shown in FIGS. 1 and 3, at least one locating foot 118 may be connected to a holdaway structure 114 having an elongate attachment portion 126 configured for mating connection with a corresponding receiver portion on the guiding shaft 108 of the landmark guiding structure 102. For example, the attachment portion 126 shown in the Figures acts as the "tongue" in the tongue-and-groove sliding connection with the groove 116 serving as the receiving portion. In this arrangement, the attachment portion 126 is longitudinally slidable with respect to the groove 116 to selectively adjust a longitudinal position of an associated locating foot 118 with respect to the landmark guiding structure 102. Through use of an auxiliary locating foot or a laterally-adjustable locating foot (not shown), the locating foot can be selectively laterally adjusted with respect to the landmark guiding structure 102.

Accordingly, through the structures shown and described herein and/or equivalents thereto, the effective or "working" position of each locating foot 118 may be adjusted in several degrees of freedom with respect to the guiding shaft 108, as desired for a particular use application of the present invention. The positions of the locating feet 118 are adjustable in order to place the guiding shaft 108 into a desired orientation with respect to an underlying surface in order to provide a guiding function to a two- or three-dimensional landmark to be associated with that underlying surface, as will now be discussed with reference to FIGS. 6-7.

As a matter of terminology, a two-dimensional landmark will be described herein as being any pen mark, bovie burn, pinprick, or other mark which indicates a location, but substantially not a trajectory, of a selected portion of the surface in a user-perceptible form—either via the user's own senses or with the assistance of a perception aid such as, but not limited to, a non-visible light spectrum illuminator. A three-dimensional landmark will be described herein as being any guide pin, Kirschner wire, guidewire, drill bit, or other item which substantially indicates both a location of a selected portion of the surface and a trajectory at which that location is penetrated by the three-dimensional landmark, again in any suitable user-perceptible form. Both two- and three-dimensional landmarks will be referenced collectively herein as "landmarks" and used without discrimination, except where the dimensionality is implicitly or explicitly indicated.

The instrument 100 of the Figures may be used to dictate at least one of a desired location and a desired trajectory for association of a landmark with an underlying surface, which will be described herein as a patient tissue surface. The use environment will be described herein as being a medical use environment, wherein a device is penetrating into a relatively stationary patient tissue, but could be any suitable environment in which a device moves in at least one dimension toward or away from a relatively stationary substrate.

The patient tissue is shown and described herein as a glenoid vault, but the patient tissue could be any desired types such as, but not limited to, hip joints, shoulder joints, knee joints, ankle joints, phalangeal joints, metatarsal joints, spinal structures, long bones, soft tissue, or any other suitable use environment for the present invention.

The desired location and/or desired trajectory may be preselected in any desired manner. For example, hand calculations and/or a software program may be used to output a desired location and/or trajectory in any suitable format for physical embodiment in the instrument 100, such as, but not limited to, the specification of predetermined desired positions for each locating foot 118 to be placed into to embody the desired location and/or trajectory. These predetermined locating foot 118 positions could, for example, be based upon preoperative images of the patient tissue acquired in any suitable manner.

One example format for such predetermined locating foot 118 positions could be a group of numerical specifications representing the lateral and longitudinal distances that the user should place the locating feet 118 into. The user may optionally replace one or more existing holdaway structures 114 or locating feet 118 on the instrument 100 with separately provided auxiliary holdaway structures and locating feet. The holdaway structure(s) 114, whether original or auxiliary/replacement, may be longitudinally adjusted with respect to the guiding shaft 108 to help place each locating foot 118 into its predetermined locating foot position. Optionally, one or more scales (not shown) could be used to assist with placement of the locating feet 118 into the predetermined locating foot position. For example, a graduated numerical scale could be marked out longitudinally along the exterior of the guiding shaft 108 and each holdaway structure 114 could slide longitudinally until reaching an indicated location along the numerical scale. It is also contemplated that some sort of setting stand or setting jig (not shown) may be used to interact with and help guide the locating feet 118 into their predetermined locating foot positions.

Regardless of how the locating feet 118 achieve the predetermined locating foot positions in the just-described process, once the locating feet are in those positions, contact between the preset locating feet and corresponding predetermined portions of the patient tissue surface will result in an orientation of the landmark guiding structure with respect to the patient tissue which dictates at least one of the desired location and the desired trajectory for association of the landmark with the patient tissue. In other words, once the locating feet have achieve the predetermined locating foot positions (however that occurs) and are placed into contact with predetermined portions of the patient tissue surface, the locating feet will hold the guiding shaft 108 in an orientation with respect to the patient tissue surface that reflects at least one of the desired location and the desired trajectory. A landmark (e.g., a marking pen, guide pin, drill bit, bovie knife, or any other landmarking tool/structure) can then be guided by the guiding shaft 108 (e.g., by being passed through the throughbore 112) and into contact with the patient tissue surface at the desired location and/or trajectory.

Figure 6:
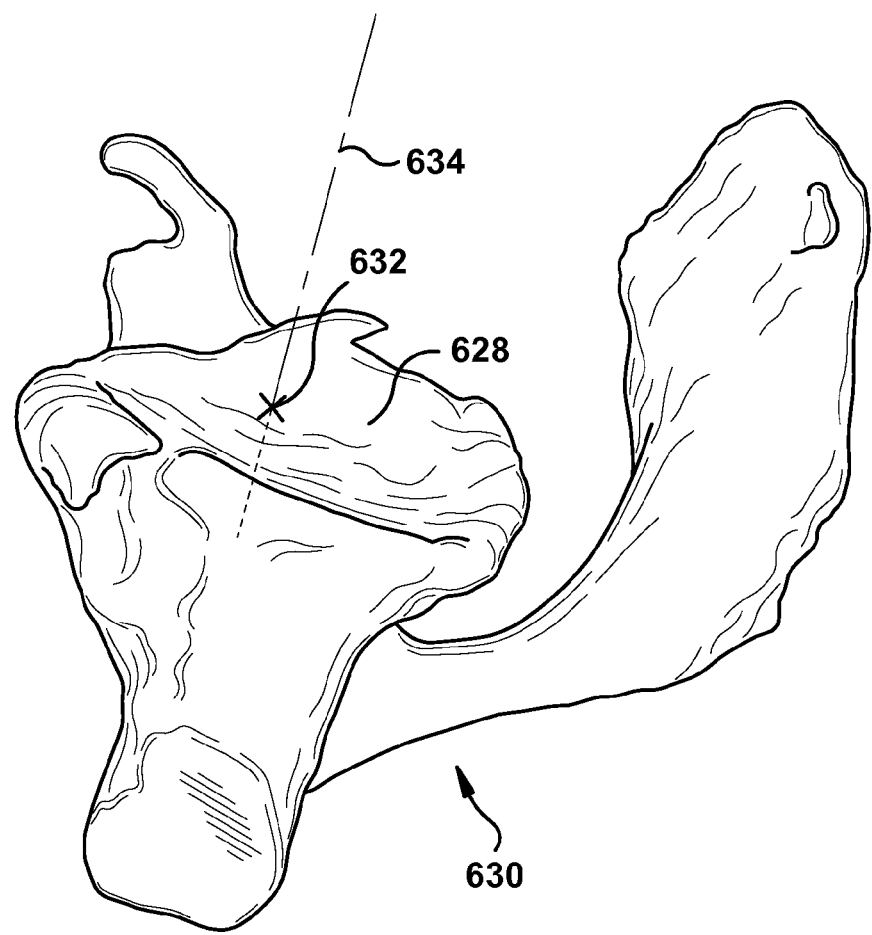
FIG. 6 is a perspective side view of a use environment of any embodiment of the present invention.

Another means of placing the landmark into contact with the patient tissue surface at the desired location and/or desired trajectory uses a reference surface 628, as shown in FIG. 6. The reference surface 628 is at least a portion of a physical model 630 substantially replicating three-dimensionally at least a portion of the patient tissue surface, and may be generated, for example, from preoperative imaging of the patient tissue surface. The reference surface 628 shown in FIG. 6 is a glenoid surface of a scapula, with only a relevant portion of the scapula being embodied in the depicted three-dimensional physical model 630.

The physical model 630 or other structure embodying a physical reference surface 628 may be provided in any suitable manner. The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the native patient tissue model may be based upon digital or analog radiography, magnetic resonance imaging, or any other suitable imaging means. A virtual patient tissue model will generally be displayed for the user to review and manipulate preoperatively, such as through the use of a computer or other graphical workstation interface. A physical model 630 may be fabricated, optionally based upon the virtual patient tissue model, as a tangible (e.g., material and palpable) representation of the physical structures at the operative site inside the patient's body by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process.

Once the physical model 630 has been manufactured and prepared for use (e.g., mechanically or chemically cleaned, cured, sterilized, or the like) using any suitable process(es), it is available for use before and/or during surgical procedures to help set up the instrument 100 for the guiding function(s) as described herein.

As shown in FIG. 6, the desired location 632 and/or desired trajectory 634 for placement of a landmark may be embodied in the physical model 630 in any suitable manner. The landmark will be described with respect to FIGS. 6-7G as a three-dimensional landmark, such as a guide pin, having both a desired location and a desired trajectory. For example, the user could "eyeball" or hand-place a landmark into association at a desired location 632 and desired trajectory 634 with respect to the reference surface 628. As another example, the physical model 630 could be manufactured with a protrusion extending out from the reference surface 628 at the desired location 632 and desired trajectory 634. As yet another example, the physical model 630 could be manufactured with an aperture (not shown) extending into the material of the physical model at the desired location 632 and desired trajectory 634, and the user could optionally temporarily or permanently place a guide pin or other elongate structure into the aperture to show the desired trajectory 634 extending outward from the reference surface 628. Regardless of how the reference surface 628 is configured, it is contemplated that the desired location 632 and desired trajectory 634 will be associated with the reference surface 628 in a manner to facilitate transfer of the relevant location and trajectory information to the instrument 100, and using the instrument, to the patient tissue surface during the surgical procedure. FIGS. 7A-7G illustrate one example of a sequence of operation for such transfer.

Figure 7A:
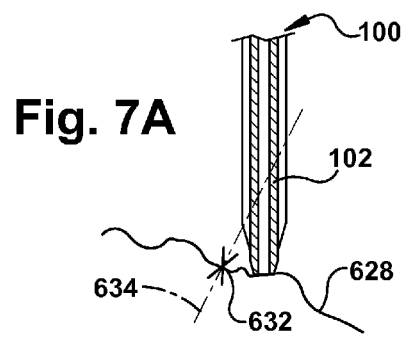
FIGS. 7A-7G schematically illustrate an example use sequence of any embodiment of the present invention.

In FIG. 7A, the desired location 632 and desired trajectory 634 have been already associated with the reference surface 628, using any of the aforementioned techniques or any other suitable means, in such a way as to be transferrable to the instrument 100. The landmark guiding structure 102 is shown as being near the reference surface 628, but has not yet been positioned to reflect the desired location 632 or desired trajectory 634.

Figure 7B:
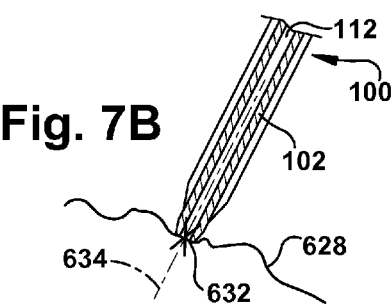

Turning to FIG. 7B, the landmark guiding structure 102 has been repositioned with respect to the reference surface 628 so that the distal guiding end 106 is located substantially at the desired location 632 and the throughbore 112 is substantially collinear with the desired trajectory 634. (Though FIGS. 7A-7G are two-dimensional schematic cross-sectional views of the described process, one of ordinary skill in the art should be able to mentally extrapolate the three-dimensional interactions based on the depicted portions of the process.) Accordingly, the instrument 100 is being held in FIG. 7B such that the throughbore 112 of the landmark guiding structure 102 reflects or embodies the desired trajectory 634, and the distal guiding end 106 reflects or embodies the desired location 632, for transfer from the reference surface 628 to the patient tissue surface.

Figure 7C:
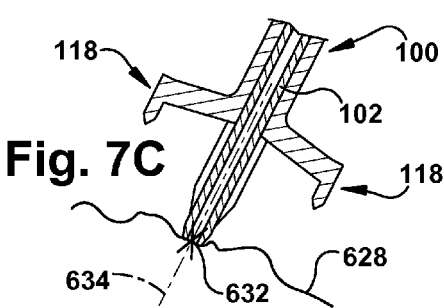

In FIG. 7C, one or more locating feet 118 have been selected and connected to the landmark guiding structure 102 via the holdaway structure 114 (optionally with a bridge region 224). The locating feet 118 are shown as having simple rectilinear shapes, but may have any desired feature(s) (e.g., anchoring spikes, traction pads) or shape(s), and may be configured to be located any desired lateral distance from the landmark guiding structure 102, as suitable for a particular application of the present invention. As depicted in FIG. 7C, the locating feet 118 are longitudinally spaced from the reference surface 628.

Figure 7D:
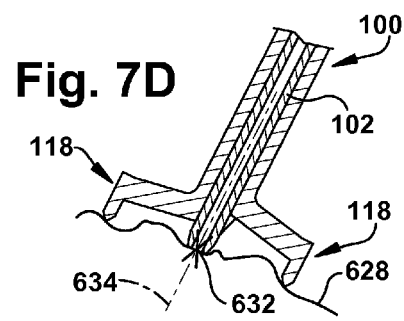

The locating feet 118 are adjusted longitudinally relative to the landmark guiding structure 102 by manipulation of the corresponding holdaway structure(s) 114 into the position shown in FIG. 7D. Though only two locating feet 118 are shown in FIGS. 7A-7G, one of ordinary skill in the art will understand that a suitable number of locating feet 118 should be used to provide reasonable certainty that the desired location 632 and desired trajectory 634 are being embodied by the instrument 100 for transfer from the reference surface 628 with a desired degree of accuracy. The locating feet 118 should each be adjusted with respect to the landmark guiding structure 102 into "guiding contact" with a particular portion of the reference surface 628.

Figure 7E:
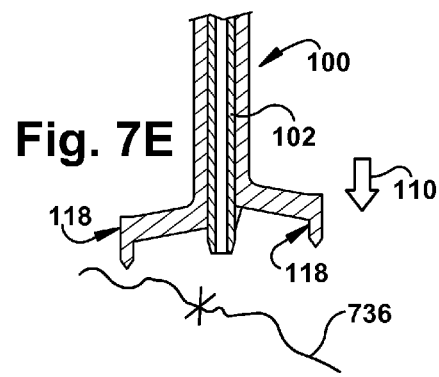
Figure 7F:
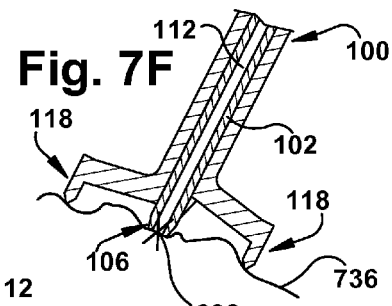

Stated differently, and as shown in FIGS. 7E-7F, when all of the locating feet 118 have achieved their respective guiding contact positions and are being maintained in those positions (e.g., through action of a locking mechanism 122), the instrument 100 will embody the desired location 632 and desired trajectory 634 in such a way that the three-dimensional positioning of the locating feet 118 in their guiding contact positions can then be placed (e.g., by lowering in the longitudinal direction 110) into corresponding positions upon the patient tissue surface 736 to transfer the desired location and desired trajectory from the reference surface 628 to the patient tissue surface. A reasonably knowledgeable user should be able to approximately replicate placement of the locating feet 118 upon the patient tissue surface 736 by visually "eyeballing" the placement. However, when an appropriate number of locating feet 118 are used, which have previously been set into the guiding contact positions through use of the reference surface 628, the landmark guiding structure 102 will likely "rock" or otherwise shift with respect to the patient tissue surface 736 upon initial contact. This action is similar to that of a table sitting on an uneven substrate and will remain until the instrument 100 has been moved slightly to more exactly place each locating foot 118 into guiding contact with a particular portion of the patient tissue surface 736 corresponding to the particular portion of the reference surface 628 which was used to "set" the instrument into the desired location 632 and the desired trajectory 634. Once a close correlation has been achieved with the positioning of the instrument 100 on the patient tissue surface 736 reflecting the positioning of the instrument on the reference surface 628, the user will likely feel that the instrument 100 seems secure and steady upon the patient tissue surface and can have reasonable confidence that the desired location 632 and desired trajectory 634 are being adequately accurately transferred or replicated from the reference surface to the patient tissue surface. This confidence arises, in part, from the unique topography of a patient tissue surface 736, which is reflected in the reference surface 628 and was used to place a suitable number of locating feet 118 into guiding contact positions.

For example, and as shown in FIG. 7F, the instrument 100 has been placed and adjusted to that the locating feet 118 squarely and firmly contact the patient tissue surface 736. Between the user's own "dead reckoning" and the positive indication provided by the close fit between the locating feet 118 and the patient tissue surface 736, the user can be fairly certain that the distal guiding end 106 is located at the desired location 632 and that a landmark inserted through the throughbore 112 will contact the patient tissue surface 736 at the desired location 632, as set with the assistance of the reference surface 628.

Figure 7G:
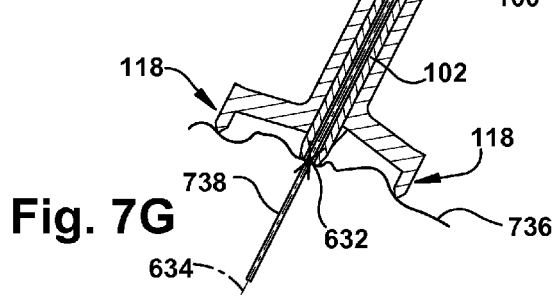

As shown in FIG. 7G, a landmark 738 has, indeed, been inserted through the throughbore 112 and penetrates into the patient tissue surface 736 at the desired trajectory 634. Optionally, the landmark 738 may have been originally positioned in the reference surface 628, as previously mentioned, and carried from the reference surface to the patient tissue surface 736 by the instrument 100.

When the landmark is a two-dimensional landmark (not shown), the trajectory may not be important, as long as the desired location 632 is transferred from the reference surface 628 to the patient tissue surface 736. However, one of ordinary skill in the art will be able to readily configure an instrument 100 having an appropriate number of locating feet 118 with suitable type, configuration, orientation, and other physical properties for a particular application of the present invention.

When the desired location 632 and/or desired trajectory 634 have been transferred from the reference surface 628 to the patient tissue surface 736, the instrument can be removed from the patient tissue surface 736. The landmark 738 remains in place and can be used for any desired purpose. The sequence of FIGS. 7A-7G may be repeated as desired to place a plurality of landmarks 738 in the same patient or in different patients, with intermediate sterilizations and reconfigurations of the instrument 100 occurring as appropriate.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described instrument 100 are merely illustrative; one of ordinary skill in the art could readily determine any number or type of components, sequences of steps, or other means/options for guiding a landmark in a manner substantially similar to those shown and described herein. Any of the described structures or components could be integrally formed as a single piece or made up of separate sub-components, with either of these formations involving any suitable stock or bespoke components and/or any suitable material or combinations of materials. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. The instrument 100 could be used with any type of landmark, temporary or permanent. The instrument 100 could be at least partially disposable or intended for one-time use, possibly by including a sacrifice feature (not shown) rendering the instrument unusable after an initial use—this may be particularly helpful in a medical use environment if the distance indicator is not intended for repeat sterilization and reuse. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for transferring at least one of location and trajectory information from a reference surface to a patient tissue surface for guiding placement of a landmark, the reference surface substantially replicating three-dimensionally at least a portion of the patient tissue surface, the apparatus comprising:
    an elongate landmark guiding structure having longitudinally spaced proximal and distal guiding ends separated by a guiding shaft and defining a longitudinal axis;
    at least two locating feet, each locating foot being laterally spaced from, and indirectly connected to, the landmark guiding structure;
    a holdaway structure connected to each locating foot, each holdaway structure being adjustably connected to the landmark guiding structure to indirectly and longitudinally adjustably attach the associated locating foot to the landmark guiding structure in a spaced-apart relationship therewith, wherein the holdaway structure comprises a first part that interacts with the landmark guiding structure and a second part that connects to the associated locating foot and extends radially outward from the longitudinal axis of the landmark guiding structure, the first and second parts being rigidly attached to one another so as to not be angularly adjustable with respect to each other; wherein at least one of the holdaway structures is longitudinally adjustable along the guiding shaft, and at least one of the locating feet is located substantially lateral to the distal guiding end; and
    a manipulation handle connected to the landmark guiding structure;
    wherein the landmark guiding structure is placed in at least one of a desired location and a desired trajectory with respect to the reference surface, each locating foot is adjusted independently from the other locating feet relative to the landmark guiding structure, via adjustment of the associated holdaway structure, into guiding contact with a particular portion of the reference surface, each locating foot is maintained in the guiding contact position, the apparatus is removed from the reference surface, and the apparatus is placed with each locating foot in guiding contact with a particular portion of the patient tissue surface corresponding to the particular portion of the reference surface such that at least one of the desired location and desired trajectory of the landmark guiding structure at the reference surface is replicated by the landmark guiding structure at the patient tissue surface.

2. The apparatus of claim 1, wherein the at least two locating feet includes at least four locating feet laterally spaced from one another, each locating foot being laterally spaced from the landmark guiding structure.

3. The apparatus of claim 1, wherein at least one of the locating feet is removable from the apparatus, the removed locating foot being selectively replaced upon the apparatus with a separately provided auxiliary locating foot having some physical property that differs from a corresponding physical property of the removed locating foot.

4. The apparatus of claim 1, wherein the landmark guiding structure guides a three-dimensional landmark into contact with the patient tissue surface in at least one of the desired location and the desired trajectory.

5. The apparatus of claim 1, wherein the landmark guiding structure guides a two-dimensional landmark into contact with the patient tissue surface in the desired location.

6. The apparatus of claim 1, including a locking mechanism to selectively maintain at least one of the locating feet in the guiding contact position during relocation of the apparatus from the reference surface to the patient tissue surface.

7. The apparatus of claim 1, wherein the landmark guiding structure carries a landmark therewith from the reference surface to the patient tissue surface.

8. A method of transferring at least one of location and trajectory information from a reference surface to a patient tissue surface, the reference surface substantially replicating at least a portion of the patient tissue surface, the method comprising the steps of:
    providing an apparatus comprising a landmark guiding structure defining a longitudinal axis;
    providing the apparatus with at least two locating feet, each locating foot being laterally spaced from, and indirectly connected to, the landmark guiding structure;
    connecting a holdaway structure to each locating foot, wherein the holdaway structure comprises a first part that interacts with the landmark guiding structure and a second part that connects to the associated locating foot and extends radially outward from the longitudinal axis of the landmark guiding structure;
    adjustably connecting each holdaway structure to the landmark guiding structure to indirectly and longitudinally adjustably attach the associated locating foot to the landmark guiding structure in a spaced-apart relationship therewith;
    providing a manipulation handle connected to the landmark guiding structure;
    placing the landmark guiding structure in at least one of a desired location and a desired trajectory with respect to the reference surface;
    adjusting each locating foot relative to the landmark guiding structure independently from the other locating feet, via adjustment of the associated holdaway structure, into guiding contact with a particular portion of the reference surface;
    maintaining each locating foot in the guiding contact position;
    removing the apparatus from the reference surface; and
    placing the apparatus with each locating foot in guiding contact with a particular portion of the patient tissue surface corresponding to the particular portion of the reference surface such that at least one of the desired location and desired trajectory of the landmark guiding structure at the reference surface is replicated by the landmark guiding structure at the patient tissue surface.

9. The method of claim 8, wherein the step of providing at least two locating feet includes the step of providing at least four locating feet laterally spaced from one another, each locating foot being laterally spaced from the landmark guiding structure.

10. The method of claim 8, including the steps of:
    removing at least one of the locating feet from the apparatus; and
    selectively replacing the removed locating foot upon the apparatus with a separately provided auxiliary locating foot having some physical property that differs from a corresponding physical property of the removed locating foot.

11. The method of claim 8, wherein the elongate landmark guiding structure has longitudinally spaced proximal and distal guiding ends separated by a guiding shaft, the method including the steps of:
configuring at least one of the holdaway structures to be longitudinally adjustable along the guiding shaft; and
locating at least one of the locating feet substantially lateral to the distal guiding end.

12. The method of claim 8, including the step of guiding a three-dimensional landmark into contact with the patient tissue surface in at least one of the desired location and the desired trajectory using the landmark guiding structure.

13. The method of claim 8, including the step of guiding a two-dimensional landmark into contact with the patient tissue surface in the desired location using the landmark guiding structure.

14. The method of claim 8, including the step of selectively maintaining at least one of the locating feet in the guiding contact position during relocation of the apparatus from the reference surface to the patient tissue surface.

15. The method of claim 8, including the step of carrying a landmark with the landmark guiding structure from the reference surface to the patient tissue surface.

16. An adjustable instrument for dictating at least one of a desired location and a desired trajectory for association of a landmark with a patient tissue, the instrument comprising:
an elongate landmark guiding structure having longitudinally spaced proximal and distal guiding ends separated by a guiding shaft and defining a longitudinal axis;
at least two holdaway structures adjustably connected to the landmark guiding structure for longitudinal motion relative to the landmark guiding structure; and
at least two locating feet, each locating foot being laterally spaced from the landmark guiding structure, each locating foot being directly connected to at least one of the at least two holdaway structures and, via the associated holdaway structure, being indirectly connected to the landmark guiding structure for longitudinal movement, independent from the other locating feet, with respect to the landmark guiding structure;
wherein each of the at least two holdaway structures comprises a first part that interacts with the landmark guiding structure and a second part that connects to the associated locating foot and extends radially outward from the longitudinal axis of the landmark guiding structure, the first and second parts being rigidly attached to one another so as to not be angularly adjustable with respect to each other; wherein at least one of the holdaway structures is longitudinally adjustable along the guiding shaft, and at least one of the locating feet is located substantially lateral to the distal guiding end; and
wherein each holdaway structure is adjustable to place the associated locating foot associated therewith into a predetermined locating foot position such that, when the locating feet have all achieved the predetermined locating foot positions, contact between each of the locating feet and corresponding predetermined portions of the patient tissue results in an orientation of the landmark guiding structure with respect to the patient tissue which dictates at least one of the desired location and the desired trajectory for association of the landmark with the patient tissue.

17. The adjustable instrument of claim 16, including a manipulation handle connected to the landmark guiding structure for grasping by a user.

18. The adjustable instrument of claim 16, wherein the at least two locating feet includes at least four locating feet laterally spaced from one another, each locating foot being substantially longitudinally adjacent to, and laterally spaced from, a distal guiding end of the landmark guiding structure.

19. The adjustable instrument of claim 16, wherein at least one of the locating feet is removable and interchangeable upon the instrument with a separately provided auxiliary locating foot having some physical property that differs from the locating foot being replaced.

20. The adjustable instrument of claim 16, wherein the first part includes an elongate attachment portion configured for mating connection with a corresponding receiver portion on the guiding shaft of the landmark guiding structure, the second part providing lateral spacing between the associated locating foot and the landmark guiding structure, and the elongate attachment portion being slidable with respect to the receiver portion to selectively adjust a longitudinal position of the associated locating foot with respect to the landmark guiding structure.

21. The adjustable instrument of claim 16, wherein the landmark guiding structure guides a three-dimensional landmark into contact with the patient tissue surface in at least one of the desired location and the desired trajectory when the locating feet have all achieved the predetermined locating foot positions and contact is made between each of the locating feet and corresponding predetermined portions of the patient tissue.

22. The adjustable instrument of claim 16, wherein the landmark guiding structure guides a two-dimensional landmark into contact with the patient tissue surface in the desired location when the locating feet have all achieved the predetermined locating foot positions and contact is made between each of the locating feet and corresponding predetermined portions of the patient tissue.

23. The adjustable instrument of claim 16, including a locking mechanism to selectively maintain at least one of the locating feet in the predetermined locating foot position.

* * * * *